United States Patent [19]

Saby

[11] Patent Number: 5,973,324

[45] Date of Patent: Oct. 26, 1999

[54] PROCESS FOR TRACKING AND MONITORING A MANUFACTURING UNIT AND/OR A NEAR-INFRARED SPECTROMETER BY MEANS OF AT LEAST ONE INDICATOR

[75] Inventor: Claude-Alain Saby, Bron, France

[73] Assignee: Elf Antar France, Courbevoie, France

[21] Appl. No.: 08/956,461

[22] Filed: Oct. 23, 1997

[30] Foreign Application Priority Data

Oct. 23, 1996 [FR] France .................................... 96 12918

[51] Int. Cl.⁶ .......................... G01D 18/00; G01N 21/35
[52] U.S. Cl. ...................................................... 250/339.07
[58] Field of Search ........................................ 250/339.07

[56] References Cited

U.S. PATENT DOCUMENTS

| | | | |
|---|---|---|---|
| 5,596,196 | 1/1997 | Cooper et al. ...................... | 250/339.12 |
| 5,668,373 | 9/1997 | Robbat, Jr. et al. ............... | 250/339.12 |
| 5,708,593 | 1/1998 | Saby et al. ................................ | 702/85 |
| 5,845,237 | 12/1998 | Puel et al. ................................ | 702/179 |

OTHER PUBLICATIONS

M.E. Camargo, R. Radharamanan, A.I. Santos, and D.G. Petry, "Spectral decomposition in statistical process control," *Computer & Industrial Engineering*, vol. 31, No. 1/2, pp. 249–252, Oct. 1996.

*Primary Examiner*—Constantine Hannaher
*Attorney, Agent, or Firm*—Oblon, Spivak, McClelland, Maier & Neustadt, P.C.

[57] ABSTRACT

A process for tracking and monitoring the operation of a unit for manufacturing a product and/or a near-infrared spectrometer fed with the product. This process includes computing at least one indicator of proper operation of the manufacturing unit and/or of the near-infrared spectrometer. A mathematical expression combines the values of work spectra and those of corresponding recomposed spectra. The evolution of these indicators is then tracked. The spectra are obtained by transformations of spectra emanating from the spectrometer and are recorded periodically. Application of this process is in the chemical, petroleum, pharmaceutical, cosmetological and agro-food industries.

20 Claims, 4 Drawing Sheets

PROCESS FOR TRACKING AND MONITORING A MANUFACTURING UNIT AND/OR A NEAR-INFRARED SPECTROMETER BY MEANS OF AT LEAST ONE INDICATOR

TECHNICAL FIELD

The present invention relates to an on-line process for tracking and monitoring a manufacturing unit with the aid of the spectra arising from a near-infrared spectrometer to which it is linked. The process of the invention also allows the tracking and monitoring of the spectrometer itself.

It finds its application in the chemical, petroleum, pharmaceutical, cosmetological and agro-food industries.

STATE OF THE PRIOR ART

The near-infrared spectrometer is generally used to determine the physical or chemical characteristics of a sample of product to be analysed withdrawn from a manufacturing unit. It is also used to track and monitor the proper operation of the manufacturing unit to which it is linked as well as its own proper operation. Calibration of the spectrometer is necessary for these uses.

This calibration consists in devising a model which represents the mathematical relation between a characteristic of the product to be analysed and the spectrum delivered by the spectrometer. The model is built by implementing multivariate statistical techniques such as principal component analysis, principal component regression, least squares regression or neural networks.

Known methods of tracking and monitoring manufacturing units or near-infrared spectrometers consist in selecting either certain elements of the spectrum, or variables arising from the computations of the modelling, and then in tracking these elements and/or these variables by means of control charts.

One of these known methods is described in French Patent Application No. 95 12087 filed on Oct. 16, 1995. This method of tracking the operation of a slave instrument and of a manufacturing unit to which it is linked comprises a procedure of multivariate calibration of a master analyser, periodic procedures for standardizing the signals delivered by the slave analyser fed with the standardizing products and a calibration transfer step during which parameters associated with a calibration transfer algorithm are computed. It consists furthermore in choosing, on the one hand, at least one of the said parameters or a mathematical combination of at least two of them as tracking and control indicator for the operation of the slave analyser and on the other hand a method of tracking and control. At the completion of each periodic standardizing procedure, the evolution over time of the value of the tracking and control indicator is monitored by applying the tracking and control method, then proper operation of the slave analyser and that of the manufacturing unit to which it is linked is ascertained by identifying the causes of the evolution of the value of the indicator from the results obtained by applying the tracking and control method and a causes/effects diagram. According to a particular characteristic of this method, the slave analyser and the master analyser are the same analyser used at different periods of time.

This method is particularly well suited to the tracking of near-infrared spectrometers. On the other hand, it does not always make it possible to distinguish the changes of production from the malfunctions of the unit to which a spectrometer is linked. It also has the drawback of requiring products with known characteristics so as to carry out the periodic standardizing procedures.

BACKGROUND OF THE INVENTION

The present invention is aimed specifically at remedying these drawbacks, and in particular at providing a process for tracking and/or monitoring the operation of a near-infrared spectrometer and the manufacturing unit to which it is linked.

By virtue of this process it is possible to expose disturbances, drifting, anomalies of operation of the spectrometer and of the associated measurement rig as well as of the manufacturing unit to which it is linked, to identify the causes of these malfunctions and to make provisions suitable for each situation: for example to declare the result of an analysis invalid and to warn the operator running the unit to which the spectrometer is linked and to supply him with elements for making his decisions.

This process finds its application in analysis laboratories and the manufacturing units of the chemical, petroleum, pharmaceutical, cosmetological and agro-food industries.

For this purpose the present invention proposes a process for tracking and monitoring by means of at least one indicator, the operation of a unit for manufacturing a product and/or a near-infrared spectrometer fed with the said product, the said spectrometer delivering spectra consisting of series of values of absorbance for various values of wavelengths, consisting in executing the following steps:

periodically recording, in the form of numerical data, spectra arising from the near-infrared spectrometer, mathematically transforming the numerical data of each recorded spectrum so as to obtain transformed spectra, constructing a string of work spectra from the values obtained previously, by selecting from each transformed spectrum, a set of consecutive wavelengths characteristic of the manufactured product, characterized in that it consists in executing the following steps also:

computing coefficients by series decomposition of each work spectrum, choosing a limited number n of coefficients by performing a selection procedure, determining a recomposed spectrum by recomposing each work spectrum from the chosen coefficients, computing at least one indicator of proper operation of the manufacturing unit and/or of the near-infrared spectrometer, by means of a mathematical expression which combines the values of each work spectrum and those of the corresponding recomposed spectrum, tracking the evolution over time of the indicator of proper operation.

According to another characteristic of the process of the invention the decomposition of the work spectra is performed by means of a series decomposition chosen from Fourier and Hadamard series and wavelet series decompositions.

According to another characteristic of the process of the invention with the string of work spectra including a first spectrum, the selection procedure consists in determining the number n of coefficients by executing the following steps:

choosing from the first work spectrum a number 1 of consecutive wavelengths, computing coefficients by series decomposition of the first spectrum, choosing the first p coefficients, determining a first recomposed spectrum by recomposing the first work spectrum from the first p coefficients, computing a parameter STDm through the formula:

$$STDm=[\Sigma_i(A_i-A'_i)^2/l]^{1/2}$$

in which:

A$_i$ represents the mathematically transformed absorbance value for wavelength i of the first work spectrum, A'$_i$ represents the mathematically transformed absorbance value for wavelength i of the first recomposed work spectrum, i varies from 1 to l, l represents the chosen number of wavelengths iteratively repeating the computation of the parameter STDm with the first p+q coefficients, q going from 1 to l/4, comparing the values STDm thus obtained with a threshold value STDs, adopting the number n of coefficients corresponding to the value STDm immediately greater than the value STDs.

According to another characteristic of the process of the invention the near-infrared spectrometer having known repeatability, the threshold value STDs is chosen equal to the standard deviation of the said repeatability.

According to another characteristic of the process of the invention the mathematical expression which combines the values of the transformed spectrum and those of the recomposed spectrum is the following:

$$STD=[\Sigma_j(A_j-A'_j)^2/l]^{1/2}$$

in which:

STD represents the indicator of proper operation,

A$_j$ represents the mathematically transformed absorbance value for wavelength j of each work spectrum, A'$_j$ represents the mathematically transformed absorbance value for wavelength j of each work spectrum recomposed with the adopted number n of coefficients, j varies from 1 to l l represents the chosen number of wavelengths.

According to another characteristic of the process of the invention in order to track the evolution over time of the indicator of proper operation, a monovariate control chart is used.

According to another characteristic of the process of the invention, a causes/effects diagram is used to track the evolution over time of the indicator of proper operation.

BRIEF DESCRIPTION OF THE DRAWINGS

The invention will be better understood on reading the description which follows, with reference to the appended drawings in which.

DETAILED ACCOUNT OF THE INVENTION

Generally, the process of the invention makes it possible to track and monitor the operation of a manufacturing unit by means of a near-infrared spectrometer. It also allows the tracking and monitoring of the operation of the spectrometer itself.

Figure 1:
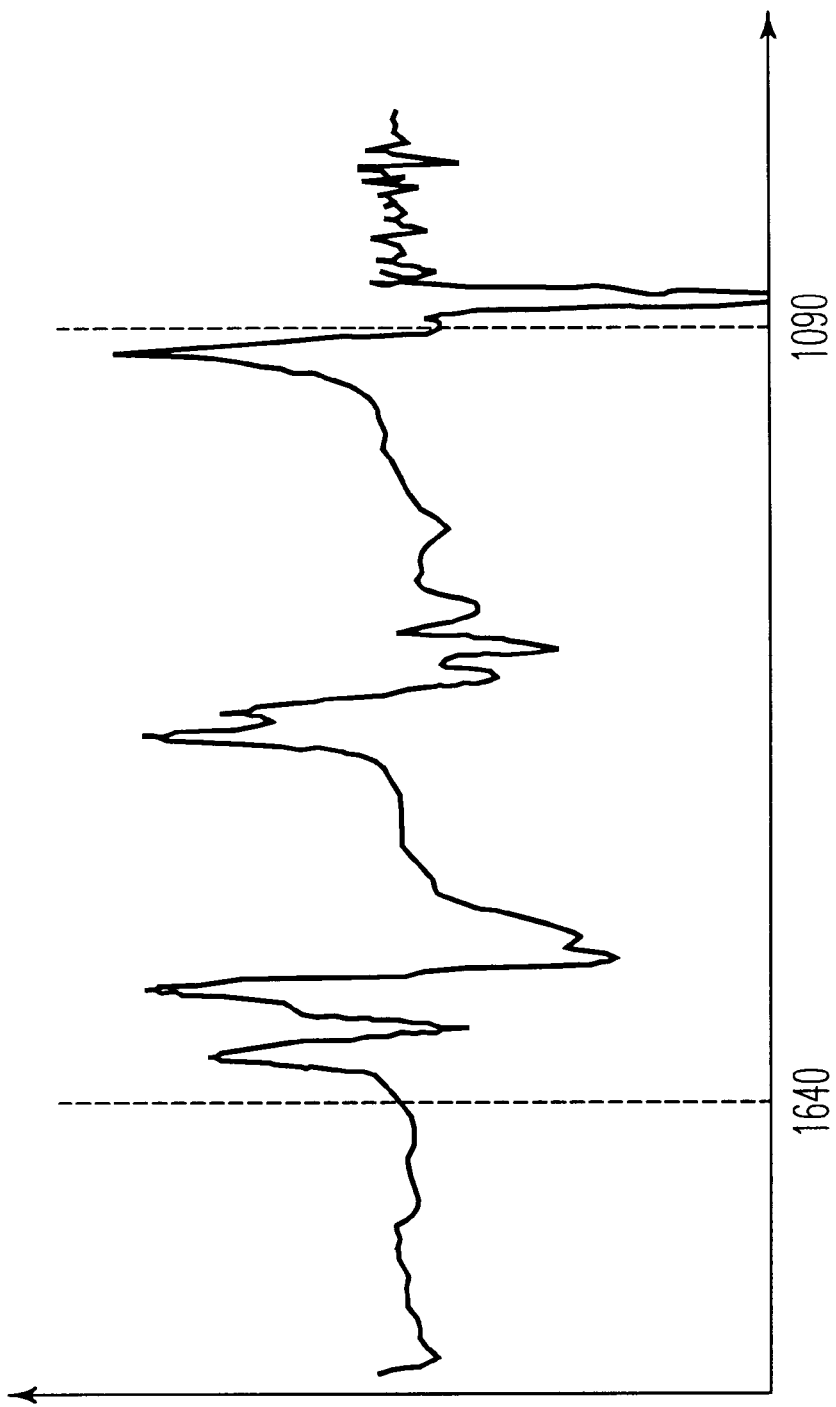
FIG. 1 represents the first derivative of a recorded spectrum emanating from a near-infrared spectrometer.
Figure 2:
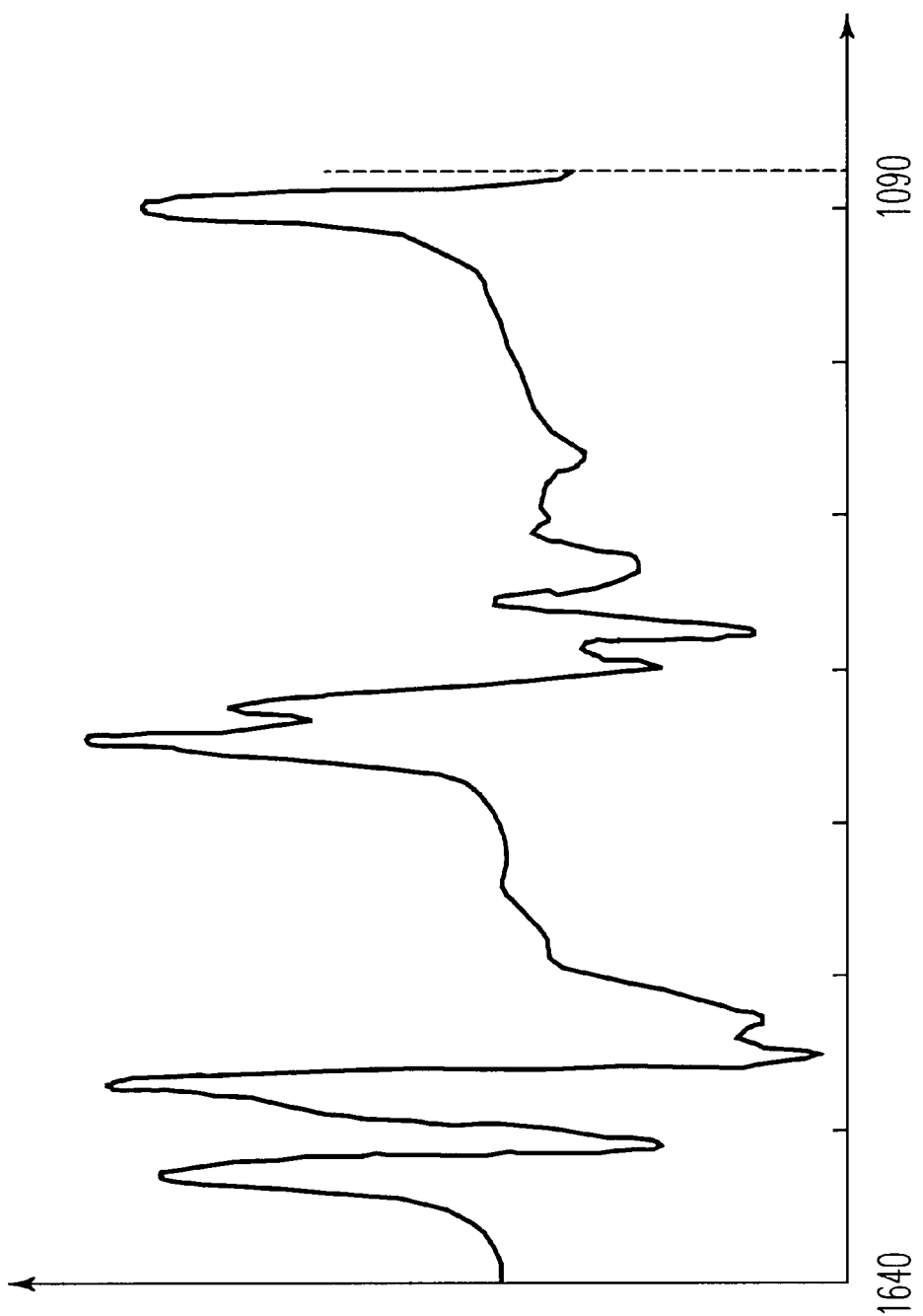
FIG. 2 represents a work spectrum.

The process of the invention used to monitor the proper operation of a production unit, for example the production of petrol in a crude oil refinery, consists in periodically recording in a computer every three mins., in the form of numerical data, the results of the measurement of absorbance of the petrol produced, by means of a near-infrared spectrometer, in the 907 nm to 1793 nm range. With a sampling spacing of 0.75 nm a set of spectra each consisting of the 1182 absorbance values measured over this range of wavelengths is thus obtained. Each spectrum is then transformed by computing the first derivative of the absorbance with respect to wavelength. An example of these spectra is represented in the diagram of FIG. 1 in which the ordinate gives the derivative values of absorbance and the abscissa gives the wavelengths. Two ranges of values of wavelengths characteristic of the petrol produced are selected from each transformed spectrum, so as to construct two work spectra:

a first work spectrum represented in FIG. 2 which comprises the derivative values of absorbance for the wavelengths lying between 1090 and 1640 nm, i.e. 735 pairs of values, a second work spectrum which comprises the derivative values of absorbance for the wavelengths lying between 1090 and 1540 nm.

These ranges of wavelengths characteristic of the manufactured product are determined experimentally.

The next step of the process of the invention consists in computing coefficients by Fourier series decomposition of the work spectra by applying the following formula:

$$F(k)=(1/N)\Sigma_i y_i \exp(-j2i\pi k/N)$$

in which:

y$_i$ represents the absorbance values of a work spectrum

F(k) represents the coefficients resulting from the Fourier series decomposition at the frequency k/N, N=735 for the first work spectrum N=600 for the second work spectrum i varies from 0 to N-1 k varies from 0 to N-1

The number of coefficients k is limited to a value n which is much lower than the value N for each work spectrum by performing the following selection procedure:

a number l of consecutive wavelengths equal to 735 is chosen from the first work spectrum coefficients are computed by Fourier series decomposition of the first work spectrum, the first 20 coefficients are chosen a first recomposed work spectrum is determined from the first 20 coefficients, a parameter STDm is computed through the formula:

$$STDm=[\Sigma_i(A_i-A'_i)^2/l]^{1/2}$$

in which:

A$_i$ represents the mathematically transformed absorbance value for wavelength i of the first work spectrum, A'$_i$ represents the mathematically transformed absorbance value for wavelength i of the first recomposed work spectrum, i varies from 1 to 735, l represents the number of wavelengths of the spectrum equal to 735 the computation of the parameter STDm is iteratively repeated with the first 20+j coefficients, j varying from 1 to 735/4, the values STDm thus obtained are compared with a threshold value STDs, the number of coefficients corresponding to the value STDm immediately greater than a threshold value STDs equal to the standard deviation of the known repeatability of the near-infrared spectrometer, i.e. $0.18 \times 10^{-3}$, is adopted as the value of n. We thus obtain n=107.

The same procedures are performed with the second work spectrum, which gives a value n=42.

This selection procedure is performed for each span of wavelengths.

The first work spectrum is recomposed by inverse Fourier transformation from the 107 coefficients adopted so as to determine a first recomposed spectrum by applying the following formula:

$$y'_i = 1/N \Sigma_k F(k) \exp(+j2\pi ik/N)$$

in which:
  $y'_i$ represents the recomposed values of the work spectrum
  N represents the number of wavelengths equal to 735 for the first work spectrum and 600 for the second work spectrum,
  k varies from 1 to 107 for the first work spectrum
  k varies from 1 to 42 for the second work spectrum
  F(k) represents the coefficients resulting from the Fourier series decomposition at the frequency 1/N.

A first indicator of proper operation of the petrol manufacturing unit is computed from the values of each first work spectrum and from the values of the recomposed work spectra, by applying the following formula:

$$STD = [\Sigma j (Aj - A'j)^2 / l]^{1/2}$$

in which:
  STD represents the first indicator of proper operation of the petrol manufacturing unit,
  Aj represents the derivative absorbance value for wavelength j of each first work spectrum,
  A'j represents the derivative absorbance value for wavelength j of each first work spectrum recomposed with the 107 chosen Fourier coefficients,
  l represents the chosen number of wavelengths equal to 735,
  j varies from 1 to l.

A second indicator of proper operation of the petrol manufacturing unit is computed from the values of each second work spectrum and from the values of the work spectra recomposed according to the same process, the value of j varying from 1 to l and the value of l being equal to 600.

A string of values is thus obtained of these two indicators at each of the instants at which the measurement of absorbance of the petrol manufactured is carried out.

If the values of these indicators evolve beyond limits deemed acceptable or in a non-random manner the operator manning the relevant manufacturing unit is alerted to the appearance of a malfunction of his unit.

Figure 3:
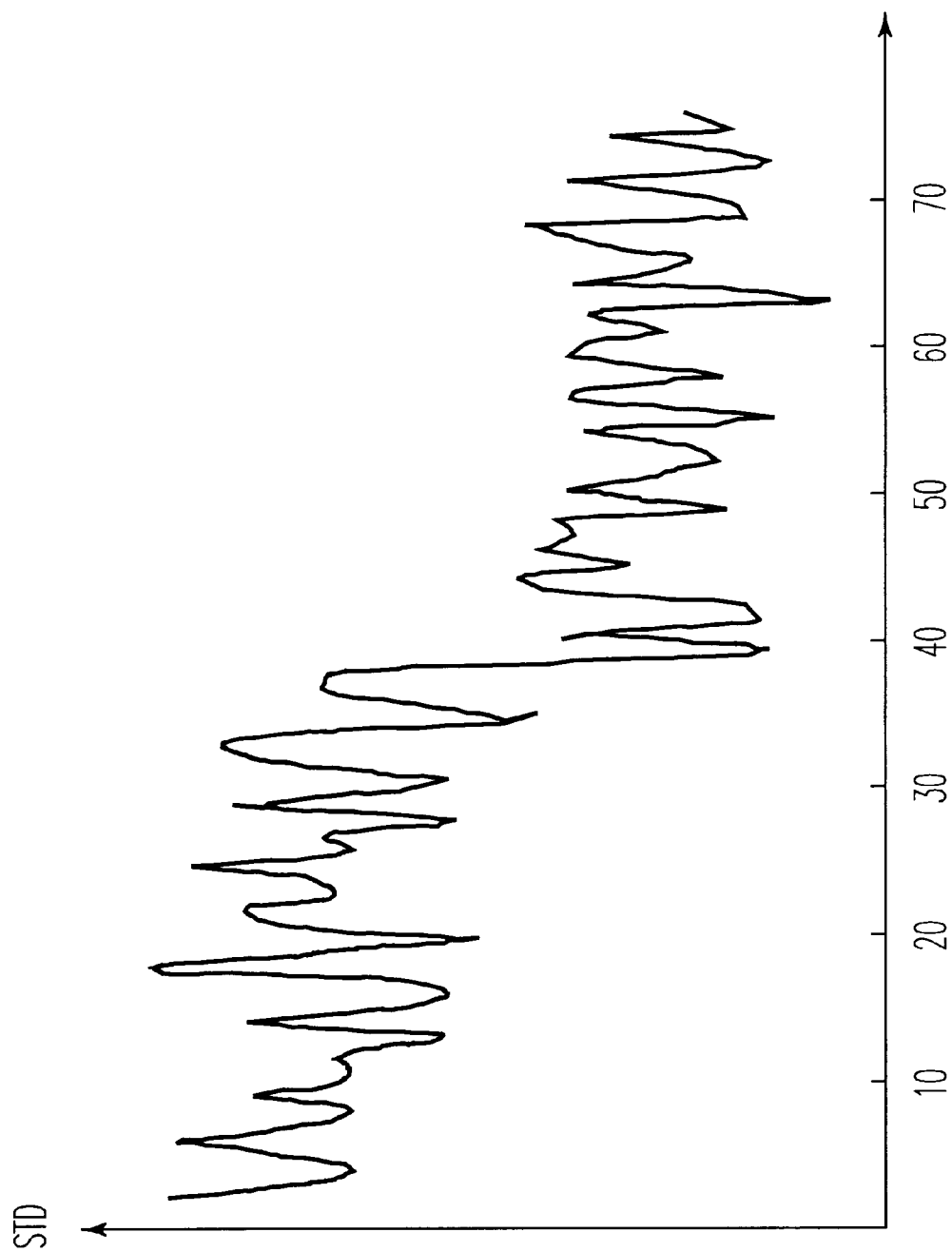
FIG. 3 represents the values of a first indicator of proper operation of a manufacturing unit at the instants of analysis of the manufactured product.

By way of example, FIG. 3 represents the value of the indicator of operation of the petrol production unit at each of the instants at which the measurement of the absorbance of the petrol produced is carried out, labelled by a sequence number, for work spectra each comprising 735 wavelengths lying between 1090 and 1640 nm uniformly distributed at a spacing of 0.75 nm, with a number of Fourier coefficients equal to 107. It is observed that the mean value of this indicator drops abruptly between the abscissae 35 and 38. This variation is characteristic of a malfunction, the origin of which may be sought by conventional methods of problem analysis.

Figure 4:
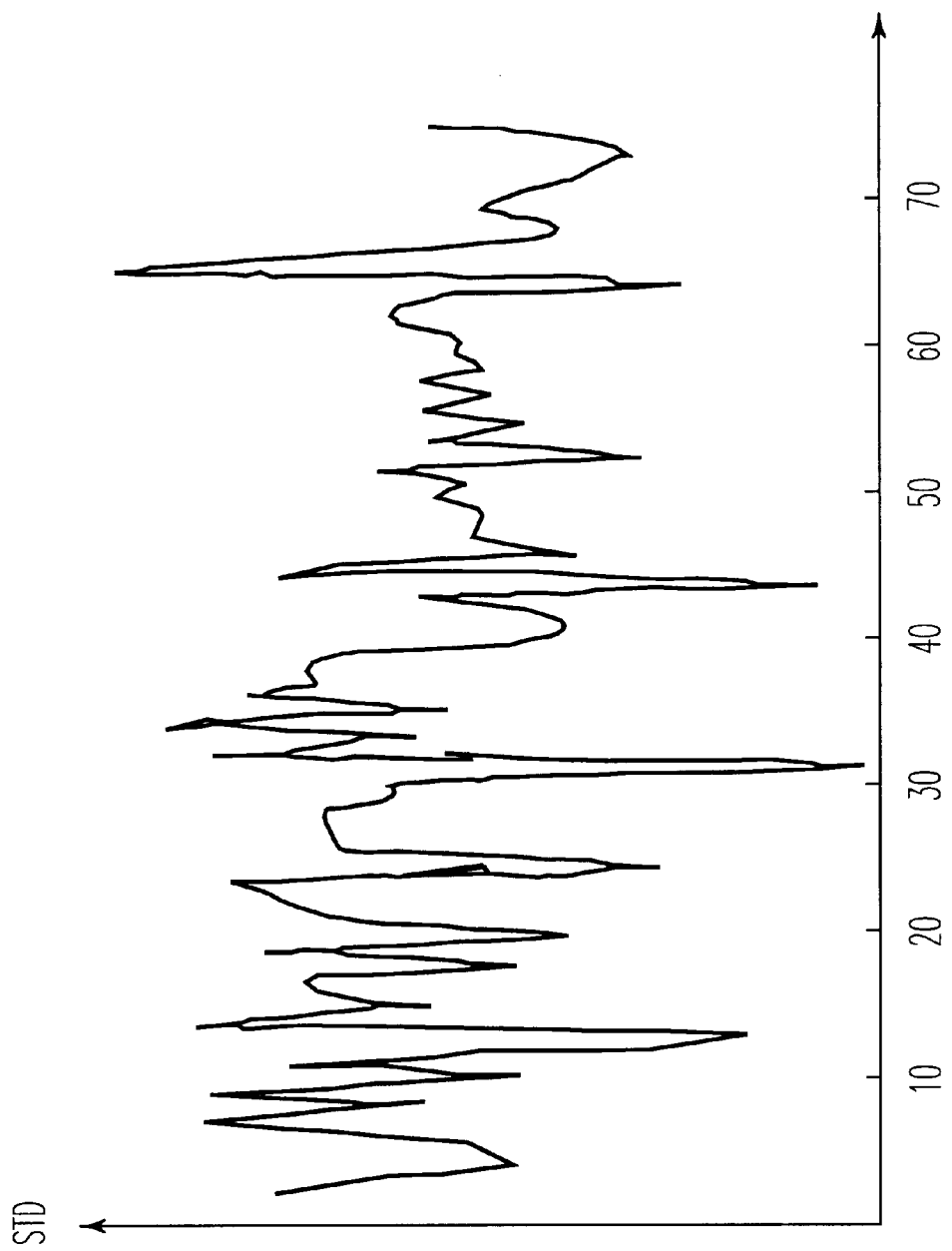
FIG. 4 represents the values of a second indicator of proper operation of a manufacturing unit at the instants of analysis of the manufactured product.

FIG. 4 reproduces the evolution over time of the indicator of operation of the unit computed with work spectra containing 600 wavelengths uniformly distributed over the range 1090 to 1540 nm at a spacing of 0.75 nm. Cyclic evolution characteristic of periodic resetting of the manufacturing unit is observed.

Each spectrum can have several characteristics STD which correspond to different wavelength spans. Thus, in the case of a malfunction, the process of the invention makes it possible to signal the suspect wavelength band.

By virtue of the displaying of the indicators of proper operation, it is possible to detect a malfunction very early, to correct the problem and thus to prevent the characteristics of the manufactured product from departing from the limits of specifications.

Another advantage of the invention is to allow the enrichment of the learning base used to devise the model, so that this base is homogeneous with a production, adaptable and devoid of spectra related to problems of operation.

In the above examples the spectrometer is considered to be operating properly.

Another aim of the process of the invention is to detect the operating defects of the near-infrared spectrometer. The manufacturing unit being considered to be correctly adjusted, the variations in the indicators of proper operation computed according to the process of the invention are representative of the malfunctions of the spectrometer.

I claim:

1. Process for tracking and monitoring the operation of a unit for manufacturing a product and/or a near-infrared spectrometer fed with the said product, the said spectrometer delivering spectra consisting of series of values of absorbance for various values of wavelengths, consisting in executing the following steps:

periodically recording, in the form of numerical data, spectra arising from the near-infrared spectrometer, mathematically transforming the numerical data of each recorded spectrum so as to obtain transformed spectra, constructing a string of work spectra from the values obtained previously, by selecting from each transformed spectrum, a set of consecutive wavelengths characteristic of the manufactured product, characterized in that it consists in executing the following steps also:

computing coefficients by series decomposition of each work spectrum, choosing a limited number n of coefficients by performing a selection procedure, determining a recomposed spectrum by recomposing each work spectrum from the chosen coefficients, computing at least one indicator of proper operation of the manufacturing unit and/or of the near-infrared spectrometer, by means of a mathematical expression which combines the values of each work spectrum and those of the corresponding recomposed spectrum, tracking the evolution over time of the indicator of proper operation.

2. Process according to claim 1, characterized in that the decomposition of the work spectra is performed by means of a series decomposition chosen from Fourier and Hadamard series and wavelet series decompositions.

3. Process according to claim 2, characterized in that, with the string of work spectra including a first spectrum, the selection procedure consists in determining the number n of coefficients by executing the following steps:

choosing from the first work spectrum a number l of consecutive wavelengths, computing coefficients by series decomposition of the first spectrum, choosing the first p coefficients, determining a first recomposed spectrum by recomposing the first work spectrum from the first p coefficients, computing a parameter STDm through the formula:

$$STDm=[\Sigma_i(A_i-A'_i)^2/l]^{1/2}$$

in which:

$A_i$ represents the mathematically transformed absorbance value for wavelength i of the first work spectrum, $A'_i$ represents the mathematically transformed absorbance value for wavelength i of the first recomposed work spectrum, i varies from 1 to l, l represents the chosen number of wavelengths iteratively repeating the computation of the parameter STDm with the first p+q coefficients, q going from 1 to l/4, comparing the values STDm thus obtained with a threshold value STDs, adopting the number n of coefficients corresponding to the value STDm immediately greater than the value STDs.

4. Process according to claim 2, characterized in that the near-infrared spectrometer having known repeatability, the threshold value STDs is chosen equal to the standard deviation of the said repeatability.

5. Process according to claim 2, characterized in that the mathematical expression which combines the values of the transformed spectrum and those of the recomposed spectrum is the following:

$$STDm=[\Sigma_j(A_j-A'_j)^2/l]^{1/2}$$

in which:

STD represents the indicator of proper operation, $A_j$ represents the mathematically transformed absorbance value for wavelength j of each work spectrum, $A'_j$ represents the mathematically transformed absorbance value for wavelength j of each work spectrum recomposed with the adopted number n of coefficients, j varies from 1 to l l represents the chosen number of wavelengths.

6. Process according to claim 2 characterized in that in order to track the evolution over time of the indicator of proper operation, a monovariate control chart is used.

7. Process according to claim 2 characterized in that in order to track the evolution over time of the indicator of proper operation, a causes/effects diagram is used.

8. Process according to claim 1, characterized in that, with the string of work spectra including a first spectrum, the selection procedure consists in determining the number n of coefficients by executing the following steps:

choosing from the first work spectrum a number l of consecutive wavelengths, computing coefficients by series decomposition of the first spectrum, choosing the first p coefficients, determining a first recomposed spectrum by recomposing the first work spectrum from the first p coefficients, computing a parameter STDm through the formula:

$$STDm=[\Sigma_i(A_i-A'_i)^2/l]^{1/2}$$

in which:

$A_i$ represents the mathematically transformed absorbance value for wavelength i of the first work spectrum, $A'_i$ represents the mathematically transformed absorbance value for wavelength i of the first recomposed work spectrum, i varies from 1 to l, l represents the chosen number of wavelengths iteratively repeating the computation of the parameter STDm with the first p+q coefficients, q going from 1 to l/4, comparing the values STDm thus obtained with a threshold value STDs, adopting the number n of coefficients corresponding to the value STDm immediately greater than the value STDs.

9. Process according to claim 8, characterized in that the near-infrared spectrometer having known repeatability, the threshold value STDs is chosen equal to the standard deviation of the said repeatability.

10. Process according to claim 8, characterized in that the mathematical expression which combines the values of the transformed spectrum and those of the recomposed spectrum is the following:

$$STDm=[\Sigma_j(A_j-A'_j)^2/l]^{1/2}$$

in which:

STD represents the indicator of proper operation, $A_j$ represents the mathematically transformed absorbance value for wavelength j of each work spectrum, $A'_j$ represents the mathematically transformed absorbance value for wavelength j of each work spectrum recomposed with the adopted number n of coefficients, j varies from 1 to l l represents the chosen number of wavelengths.

11. Process according to claim 8 characterized in that in order to track the evolution over time of the indicator of proper operation, a monovariate control chart is used.

12. Process according to claim 8 characterized in that in order to track the evolution over time of the indicator of proper operation, a causes/effects diagram is used.

13. Process according to claim 1, characterized in that the near-infrared spectrometer having known repeatability, the threshold value STDs is chosen equal to the standard deviation of the said repeatability.

14. Process according to claim 13, characterized in that the mathematical expression which combines the values of the transformed spectrum and those of the recomposed spectrum is the following:

$$STDm=[\Sigma_j(A_j-A'_j)^2/l]^{1/2}$$

in which:

STD represents the indicator of proper operation, $A_j$ represents the mathematically transformed absorbance value for wavelength j of each work spectrum, $A'_j$ represents the mathematically transformed absorbance value for wavelength j of each work spectrum recomposed with the adopted number n of coefficients, j varies from 1 to l l represents the chosen number of wavelengths.

15. Process according to claim 13 characterized in that in order to track the evolution over time of the indicator of proper operation, a monovariate control chart is used.

16. Process according to claim 13 characterized in that in order to track the evolution over time of the indicator of proper operation, a causes/effects diagram is used.

17. Process according to claim 1, characterized in that the mathematical expression which combines the values of the transformed spectrum and those of the recomposed spectrum is the following:

$$STD=[\Sigma_j(A_j-A'_j)^2/l]^{1/2}$$

in which:

STD represents the indicator of proper operation, $A_j$ represents the mathematically transformed absorbance value for wavelength j of each work spectrum, $A'_j$ represents the mathematically transformed absorbance value for wavelength j of each work spectrum recomposed with the adopted number n of coefficients, j varies from 1 to l l represents the chosen number of wavelengths.

18. Process according to claim 17 characterized in that in order to track the evolution over time of the indicator of proper operation, a monovariate control chart is used.

19. Process according to claim 1 characterized in that in order to track the evolution over time of the indicator of proper operation, a monovariate control chart is used.

20. Process according to claim 1 characterized in that in order to track the evolution over time of the indicator of proper operation, a causes/effects diagram is used.

* * * * *